United States Patent
Deych et al.

(10) Patent No.: US 10,761,219 B2
(45) Date of Patent: Sep. 1, 2020

(54) DETECTOR ARRAY FOR RADIATION IMAGING MODALITY

(71) Applicant: ANALOGIC CORPORATION, Peabody, MA (US)

(72) Inventors: Ruvin Deych, Peabody, MA (US); Martin Choquette, Peabody, MA (US); Christopher David Tibbetts, Peabody, MA (US)

(73) Assignee: Analogic Corporation, Peabody, MA (US)

(*) Notice: Subject to any disclaimer, the term of this patent is extended or adjusted under 35 U.S.C. 154(b) by 0 days.

(21) Appl. No.: 15/781,252

(22) PCT Filed: Dec. 28, 2015

(86) PCT No.: PCT/US2015/067662
§ 371 (c)(1),
(2) Date: Jun. 4, 2018

(87) PCT Pub. No.: WO2017/116392
PCT Pub. Date: Jul. 6, 2017

(65) Prior Publication Data
US 2018/0356538 A1    Dec. 13, 2018

(51) Int. Cl.
*G01T 1/20* (2006.01)
*G01T 1/24* (2006.01)
*A61B 6/00* (2006.01)

(52) U.S. Cl.
CPC .......... *G01T 1/2006* (2013.01); *A61B 6/4035* (2013.01); *A61B 6/482* (2013.01); *G01T 1/2018* (2013.01); *G01T 1/242* (2013.01)

(58) Field of Classification Search
CPC ... G01T 1/2018; G01T 1/1603; G01T 1/2006; G01T 1/208; G01T 1/17; G01T 1/243;
(Continued)

(56) References Cited

U.S. PATENT DOCUMENTS 5,548,123 A *  8/1996  Perez-Mendez ...... G01T 1/2018
                                                       250/370.09
9,244,180 B2 *  1/2016  Frisch .................... G01T 1/208
(Continued)

FOREIGN PATENT DOCUMENTS

DE    102012215818 A1    3/2014
EP       2395373 A2    12/2011
(Continued)

OTHER PUBLICATIONS

Patent Cooperation Treaty (PCT) International Search Report and Written Opinion issued in PCT International Application No. PCT/US2015/067662, International Filing Date of Dec. 28, 2015, dated Sep. 6, 2016 (15 pgs).

*Primary Examiner* — Taeho Jo
(74) *Attorney, Agent, or Firm* — TraskBritt

(57) ABSTRACT

A dual-energy detector array for a radiation system is provided. The dual-energy detector array includes a circuit board assembly having a first side and a second side. A first conversion package is coupled to the first side of the circuit board assembly and has a first effective photon energy. A second conversion package is coupled to the second side of the circuit board assembly and has a second effective photon energy different than the first effective photon energy. A radiation filtering material is disposed within the circuit board assembly between the first conversion package and the second conversion package. The radiation filtering material attenuates at least some of the radiation photons impinging thereon.

17 Claims, 5 Drawing Sheets

(58) Field of Classification Search
CPC ....... G01T 1/242; A61B 6/482; A61B 6/4241; A61B 6/4035
USPC .................................................. 250/370.01
See application file for complete search history.

(56) References Cited

U.S. PATENT DOCUMENTS

| | | | | |
|---|---|---|---|---|
| 2007/0114426 A1* | 5/2007 | Tkaczyk | ............... | G01T 1/2018 250/370.09 |
| 2007/0235655 A1* | 10/2007 | Rhiger | ................. | G01T 1/2928 250/370.13 |
| 2008/0240339 A1* | 10/2008 | Du | ............................ | G01T 1/20 378/5 |
| 2008/0253507 A1* | 10/2008 | Levene | ................. | G01T 1/2018 378/19 |
| 2008/0315106 A1* | 12/2008 | Buchinsky | ............. | A61B 6/032 250/370.09 |
| 2009/0084960 A1* | 4/2009 | Green | ................. | G01V 5/0016 250/361 R |
| 2009/0129538 A1* | 5/2009 | Tkaczyk | ................ | A61B 6/032 378/5 |
| 2011/0095191 A1* | 4/2011 | Takihi | ................... | G01T 1/2018 250/366 |
| 2011/0192983 A1* | 8/2011 | Yu | .......................... | G01T 1/243 250/370.01 |
| 2011/0215250 A1* | 9/2011 | Ohta | ........................ | G01T 1/24 250/370.08 |
| 2011/0303849 A1* | 12/2011 | Tredwell | ............... | G01T 1/2018 250/362 |
| 2013/0075618 A1* | 3/2013 | Takihi | ................... | G01T 1/2006 250/366 |
| 2014/0183369 A1* | 7/2014 | Frisch | .................... | G01T 1/363 250/366 |
| 2017/0115406 A1* | 4/2017 | Li | ......................... | G01T 1/2018 |
| 2017/0322321 A1* | 11/2017 | Weedon | ................. | G01N 23/04 |

FOREIGN PATENT DOCUMENTS

| | | | | | |
|---|---|---|---|---|---|
| JP | | 2014035249 | * | 2/2014 | |
| JP | | 2014035249 A | | 2/2014 | |
| WO | WO-2014037247 | | * | 3/2014 | ............ G01T 1/242 |
| WO | WO-2014037247 A1 | | * | 3/2014 | ............ G01T 1/242 |

\* cited by examiner

DETECTOR ARRAY FOR RADIATION IMAGING MODALITY

CROSS-REFERENCE TO RELATED APPLICATIONS

This application is a national phase entry under 35 U.S.C. § 371 of International Patent Application PCT/US2015/067662, filed Dec. 28, 2015, designating the United States of America and published in English as International Patent Publication WO 2017/116392 A1 on Jul. 6, 2017.

BACKGROUND

The present application relates to measuring radiation attenuation by an object exposed to radiation. It finds particular application in the field of computed tomography (CT) imaging utilized in medical, security, and/or industrial applications, for example. However, it also relates to other radiation imaging modalities where converting radiation energy into electrical signals may be useful, such as for imaging and/or object detection.

Today, CT and other imaging modalities (e.g., mammography, digital radiography, etc.) are useful to provide information, or images, of interior features of an object under examination. Generally, the object is exposed to polychromatic radiation comprising photons (e.g., such as x-rays, gamma rays, etc.), and an image(s) is formed based upon the radiation absorbed and/or attenuated by the interior features of the object, or rather a number of radiation photons that are able to pass through the object. Generally, highly dense features of the object absorb and/or attenuate more radiation than less dense features, and thus a feature having a higher density, such as a bone or metal, for example, will be apparent when surrounded by less dense features, such as muscle or clothing.

The detector array typically comprises a plurality of detector cells, respectively configured to convert detected radiation into electrical signals. Based upon the number of radiation photons detected by respective detector cells and/or the electrical charge generated by respective detector cells between samplings, images can be reconstructed that are indicative of the density, effective atomic number (z), shape, and/or other properties of the object and/or features thereof.

Conventionally, radiation imaging systems employed a single energy scanner, which measures the attenuation of an integrated radiation spectrum and provides the density information of the object or rather features comprised therein. Using this density information respective features can be identified and/or classified (e.g., as a potential threat or non-threat item). While measuring the densities of the features has proven to be a useful tool for identification of the features, density information is sometimes insufficient. For example, some items of interest (e.g., threat items, tumors, etc.) may have substantially similar densities and shapes as items that are not of interest, which may make it difficult to identify some items based merely upon the measured density.

More recently, some radiation imaging systems have begun to use dual-energy scanners, which measure both the density and effective atomic number (z), of features within the object. In this way, items can be identified and/or classified based upon density and/or chemical makeup information, for example. Applications for dual-energy scanners may comprise, but are not limited to, bone densitometry, explosive detection, and/or quantitative computed tomography (CT).

Dual-energy imaging systems generally measure the absorption characteristics of features within the object under examination for a plurality of energy spectra (e.g., a higher energy spectrum and a lower energy spectrum). This approach is made possible because radiation undergoes different types of interactions with matter at different energies. In the diagnostic range of radiation energies up to 200 keV, for example, radiation interacts with matter primarily through Compton scattering and photoelectric interactions. These two types of interactions depend differently on the energy of the incident radiation. The cross-section for Compton scattering is proportional to the electron density of the object, while the photoelectric cross-section is proportional to the electron density times the atomic number cubed. Thus, by separately measuring radiation attenuation at two or more different energy spectra, the Compton scattering and photoelectric interactions can be independently measured. Based upon these independent measurements, density and effective atomic number (z) for items comprised in the object under examination can be determined.

One technique for obtaining such measurements is known as "source switching." In source switching, the energy spectrum of the radiation is switched between at least two distinguished or different energy spectra. This may be done through a variety of procedures. In one procedure, the voltage applied to a radiation source is varied causing the emitted radiation's energy to vary with the change in voltage. In another procedure, two or more spatially separated sources are configured to alternate radiation emissions (e.g., by alternating power to the sources). Where there are two energy sources, for example, one of the sources may be configured to emit radiation within a first, higher energy spectrum while the other may be configured to emit radiation within a second, lower energy spectrum.

Another technique uses a dual-energy, indirect conversion detector array (e.g., generally of sandwich type design) that comprises two scintillators and two photodetectors. A first scintillator and photodetector are configured to measure object attenuation at a first effective photon energy (e.g., where the first effective photon energy corresponds to a mean energy detected by the first scintillator) and a second scintillator and photodetector are configured to measure object attenuation at a second effective photon energy (e.g., where the second effective photon energy corresponds to a mean energy detected by the second scintillator).

BRIEF SUMMARY

Aspects of the present application address the above matters, and others. According to one aspect, a dual-energy detector array for a radiation system is provided. The dual-energy detector array comprises a circuit board assembly having a first side and a second side. The dual-energy detector array comprises a first conversion package coupled to the first side of the circuit board assembly and having a first effective photon energy. The dual-energy detector array also comprises a second conversion package coupled to the second side of the circuit board assembly and having a second effective photon energy. The dual-energy detector array further comprises a radiation filtering material disposed within the circuit board assembly between the first conversion package and the second conversion package. The radiation filtering material is configured to attenuate at least some of the radiation photons impinging thereon.

According to another aspect, a dual-energy detector array for a radiation system comprises a circuit board assembly having a first side and a second side. The dual-energy detector array comprises a second circuit board assembly having a third side and a fourth side. The dual-energy detector array comprises a first conversion package coupled to the first side of the circuit board assembly and having a first effective photon energy. The dual-energy detector array also comprises a second conversion package coupled to the fourth side of the second circuit board assembly and having a second effective photon energy. The dual-energy detector array further comprises a radiation filtering material coupled to the second side of the circuit board assembly and the third side of the second circuit board assembly. The radiation filtering material is disposed between the first conversion package and the second conversion package. The radiation filtering material is configured to attenuate at least some of the radiation photons impinging thereon.

According to another aspect, a dual-energy detector array for a radiation system comprises a circuit board assembly having a first side and a second side. The dual-energy detector array comprises a second circuit board assembly having a third side and a fourth side. The third side of the second circuit board assembly is coupled to the second side of the circuit board assembly. The dual-energy detector array comprises a first conversion package coupled to the first side of the circuit board assembly and having a first effective photon energy. The dual-energy detector array also comprises a second conversion package coupled to the second circuit board assembly and having a second effective photon energy. The dual-energy detector array further comprises a radiation filtering material disposed within the circuit board assembly between the first conversion package and the second conversion package. The radiation filtering material is configured to attenuate at least some of the radiation photons impinging thereon.

According to another aspect, a radiation system comprises a radiation source configured to emit radiation photons. The radiation system comprises a dual-energy detector array comprising a circuit board assembly having a first side and a second side. The circuit board assembly comprises a first conversion package coupled to the first side of the circuit board assembly and having a first effective photon energy. The circuit board assembly also comprises a second conversion package coupled to the second side of the circuit board assembly and having a second effective photon energy. The circuit board assembly further comprises a radiation filtering material disposed within the circuit board assembly between the first conversion package and the second conversion package. The radiation filtering material is configured to attenuate at least some of the radiation photons impinging thereon.

Those of ordinary skill in the art will appreciate still other aspects of the present application upon reading and understanding the appended description.

BRIEF DESCRIPTION OF THE DRAWINGS

The application is illustrated by way of example and not limitation in the figures of the accompanying drawings, in which like references generally indicate similar elements and in which.

DETAILED DESCRIPTION

Figure 1:
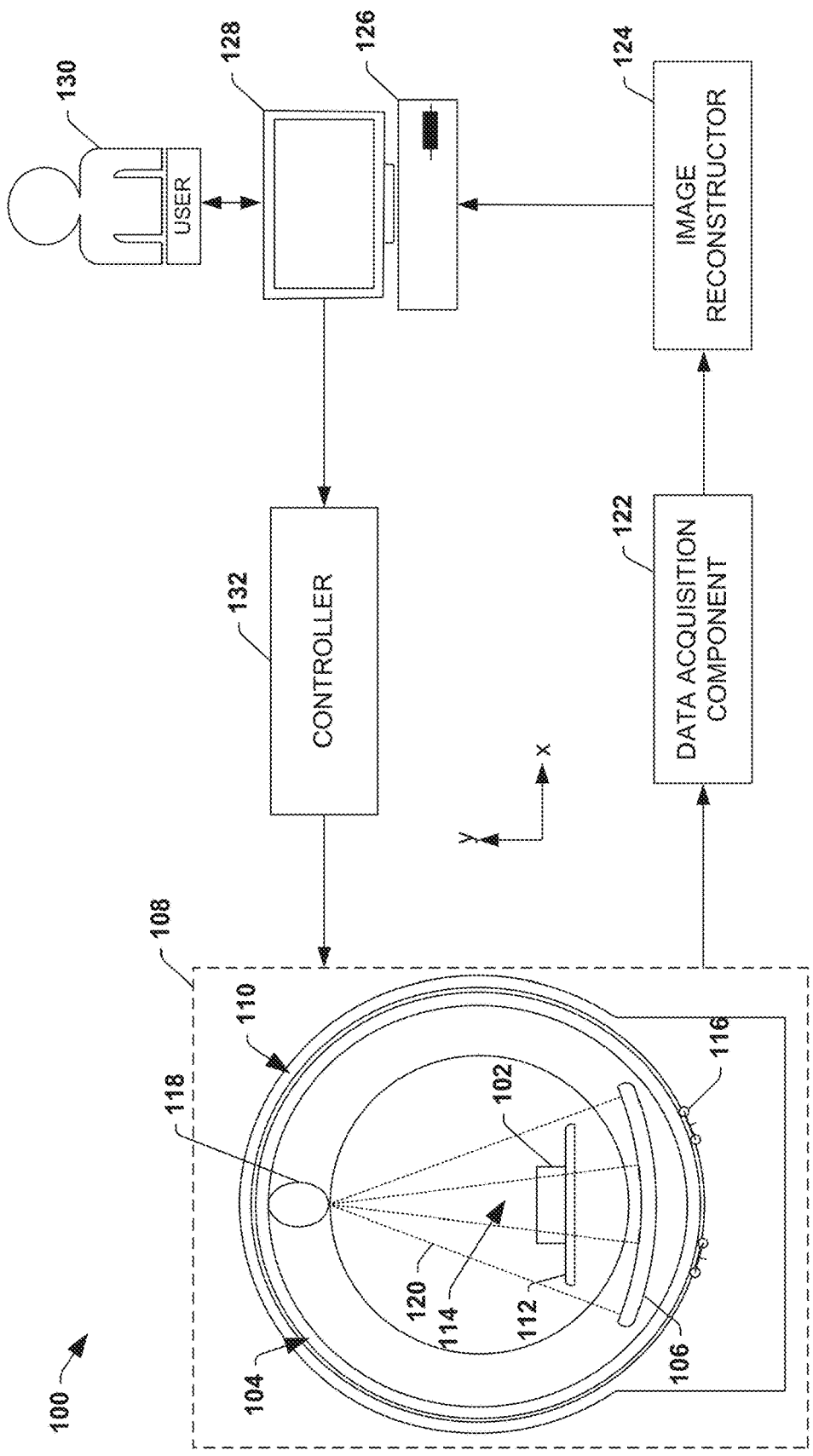
FIG. 1 illustrates an example environment of a radiation imaging modality.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

Among other things, a dual-energy detector array for a radiation system is provided herein. In some examples, the dual-energy detector array comprises a circuit board assembly, a first conversion package coupled to a first side of the circuit board assembly, and a second conversion package coupled to a second side of the circuit board assembly. As will be described in more detail below, due to among other things, a relative position between the first conversion package and the second conversion package, the first conversion package has a first effective photon energy and the second conversion package has a second effective photon energy. As used herein, an effective photon energy refers to a mean energy that is detected/measured by the conversion package. In some embodiments, the first conversion package and the second conversion package may be physically configured to detect a same radiation energy spectrum (e.g., a thickness of a radiation conversion material (e.g., scintillator or direct conversion material) of the first conversion package may be equal to a thickness of a radiation conversion material of the second conversion package; the radiation conversion material of the first conversion package may have a same material composition as the radiation conversion material of the second conversion package, etc.). However, due to the placement of the second conversion package relative to the first conversion package, the effective photon energy (e.g., mean energy) of the first conversion package may be different than the effective photon energy (e.g., mean energy) of the second conversion package. In still other embodiments, the first conversion package may be physically different than the second conversion package. As such, the physical differences, in combination with the placement of the second conversion package relative to the first conversion package, may cause the first conversion package to have a different effective photon energy than the second conversion package.

In some embodiments, the first conversion package and second conversion package are aligned with respect to direction of sampled radiation, so that the second conversion package samples (e.g., detects or measures) radiation filtered by the first radiation package. The first conversion package is configured to partially absorb the incident radiation, while the second conversion package is configured to absorb at least some of the incident radiation transmitted through the first conversion package. Because the second conversion package samples radiation filtered by the first conversion package, the effective photon energy of the first conversion package may be less than the effective photon energy of the second conversion package (e.g., because lower energy photons within an emitted spectrum are filtered by the first conversion package). Thus the first conversion package may be referred to as a Low Energy (LE) detector, and the second conversion package may be referred to as a High Energy (HE) detector. Low Energy detectors and High Energy detectors provide measurement of the object attenuation at two different effective photon energies, and therefore allow the measurement of both density and atomic number of the scanned objects.

In an example, a radiation filtering material can be disposed within the circuit board assembly between the first conversion package and the second conversion package. The radiation filtering material can attenuate at least some of the radiation photons impinging thereon to further distance the effective photon energy of the first conversion package from the effective photon energy of the second conversion package. In some examples, a single circuit board assembly can support the first conversion package, the second conversion package, and the radiation filtering material.

FIG. 1 is an illustration of an example environment 100 comprising an example radiation imaging modality that may be configured to generate data (e.g., images) representative of an object(s) 102 or features(s) thereof under examination. It will be appreciated that the features described herein may find applicability to other radiation imaging modalities besides the example computed tomography (CT) scanner illustrated in FIG. 1. Moreover, the arrangement of components and/or the types of components included in the example environment 100 are for illustrative purposes only. For example, as will be described in more detail below, at least a portion of a data acquisition component 122 may be comprised within a dual-energy detector array 106.

In the example environment 100, an examination unit 108 of the radiation imaging modality is configured to examine one or more objects 102. The examination unit 108 can comprise a rotating gantry 104 and a (stationary) support structure 110 (e.g., which may encase and/or surround as least a portion of the rotating gantry 104 (e.g., as illustrated with an outer, stationary ring, surrounding an outside edge of an inner, rotating ring)). During an examination of the object(s) 102, the object(s) 102 can be placed on a support article 112, such as a bed or conveyor belt, for example, that is selectively positioned in an examination region 114 (e.g., a hollow bore in the rotating gantry 104), and the rotating gantry 104 can be rotated about the object(s) 102 by a rotator 116, such as a motor, drive shaft, chain, roller truck, etc.

The rotating gantry 104 may surround a portion of the examination region 114 and may comprise one or more radiation sources 118 (e.g., an ionizing x-ray source, gamma radiation source, etc.) and the dual-energy detector array 106, which comprises a plurality of pixels (e.g., also referred to as detector cells). The dual-energy detector array 106 is mounted on a substantially diametrically opposite side of the rotating gantry 104 relative to the radiation source(s) 118.

During an examination of the object(s) 102, the radiation source(s) 118 emits fan- or cone-shaped radiation 120 configurations from a focal spot(s) of the radiation source(s) 118 into the examination region 114. It will be appreciated that such radiation 120 may be emitted substantially continuously and/or may be emitted intermittently (e.g., a brief pulse of radiation is emitted followed by a resting period during which the radiation source 118 is not activated).

As the emitted radiation 120 traverses the object(s) 102, the radiation 120 may be attenuated differently by different features of the object(s) 102. Because different features attenuate different percentages of the radiation 120, an image(s) may be generated based upon the attenuation, or variations in the number of photons that are detected by the dual-energy detector array 106. For example, more dense features of the object(s) 102, such as a bone or metal plate, may attenuate more of the radiation 120 (e.g., causing fewer photons to strike the dual-energy detector array 106) than less dense features, such as skin or clothing. Such images may also or instead be generated based upon the effective atomic number (z) of features, as determined by an amount of lower energy radiation traversing the feature in comparison to an amount of high energy radiation traversing the feature.

The dual-energy detector array 106 can comprise a linear (e.g., one-dimensional) or two-dimensional array of pixels disposed as a single row/column or multiple rows/columns. The pixels may directly and/or indirectly convert detected radiation into analog signals. For example, respective pixels may comprise a direct conversion material configured to convert radiation energy directly into electrical energy. As another example, respective pixels may comprise a scintillator material configured to convert radiation energy into light energy and an array of photodetectors configured to convert the light energy into electrical energy.

Signals that are produced by the dual-energy detector array 106 may be transmitted to a data acquisition component 122 that is in operable communication with the dual-energy detector array 106 (e.g., and at least portions of which may be coupled to and/or comprised within at least some of the pixels of the dual-energy detector array 106). Typically, the data acquisition component 122 is configured to convert the electrical signals output by respective pixels of the detector array into digital data and/or to combine the digital data acquired during a measuring interval. The collection of digital output signals for a measuring interval may be referred to as a "projection" or a "view". Moreover, an angular orientation of the rotating gantry 104 (e.g., and the corresponding angular orientations of the radiation source(s) 118 and the dual-energy detector array 106) relative to the object(s) 102 and/or support article 112, for example, during generation of a projection may be referred to as the "projection angle."

The example environment 100 also illustrates an image reconstructor 124 that is operably coupled to the data acquisition component 122 and is configured to generate one or more images representative of the object(s) 102 under examination based at least in part upon signals output from the data acquisition component 122 using suitable analytical, iterative, and/or other reconstruction technique (e.g., tomosynthesis reconstruction, back-projection, iterative reconstruction, etc.). Such images may be 3D images and/or 2D images.

The example environment 100 also includes a terminal 126, or workstation (e.g., a computer), configured to receive image(s) from the image reconstructor 124, which can be displayed on a monitor 128 to a user 130 (e.g., security personnel, medical personnel, etc.). In this way, the user 130 can inspect the image(s) to identify areas of interest within the object(s) 102. The terminal 126 can also be configured to receive user input which can direct operations of the examination unit 108 (e.g., a speed of gantry rotation, an energy level of the radiation, etc.).

In the example environment 100, a controller 132 is operably coupled to the terminal 126. In an example, the controller 132 is configured to receive user input from the terminal 126 and generate instructions for the examination unit 108 indicative of operations to be performed.

It will be appreciated that the example component diagram is merely intended to illustrate one embodiment of one type of imaging modality and is not intended to be interpreted in a limiting manner. For example, the functions of one or more components described herein may be separated into a plurality of components and/or the functions of two or more components described herein may be consolidated into merely a single component. Moreover, the imaging modality may comprise additional components to perform additional features, functions, etc. (e.g., such as automatic threat detection).

Figure 2:
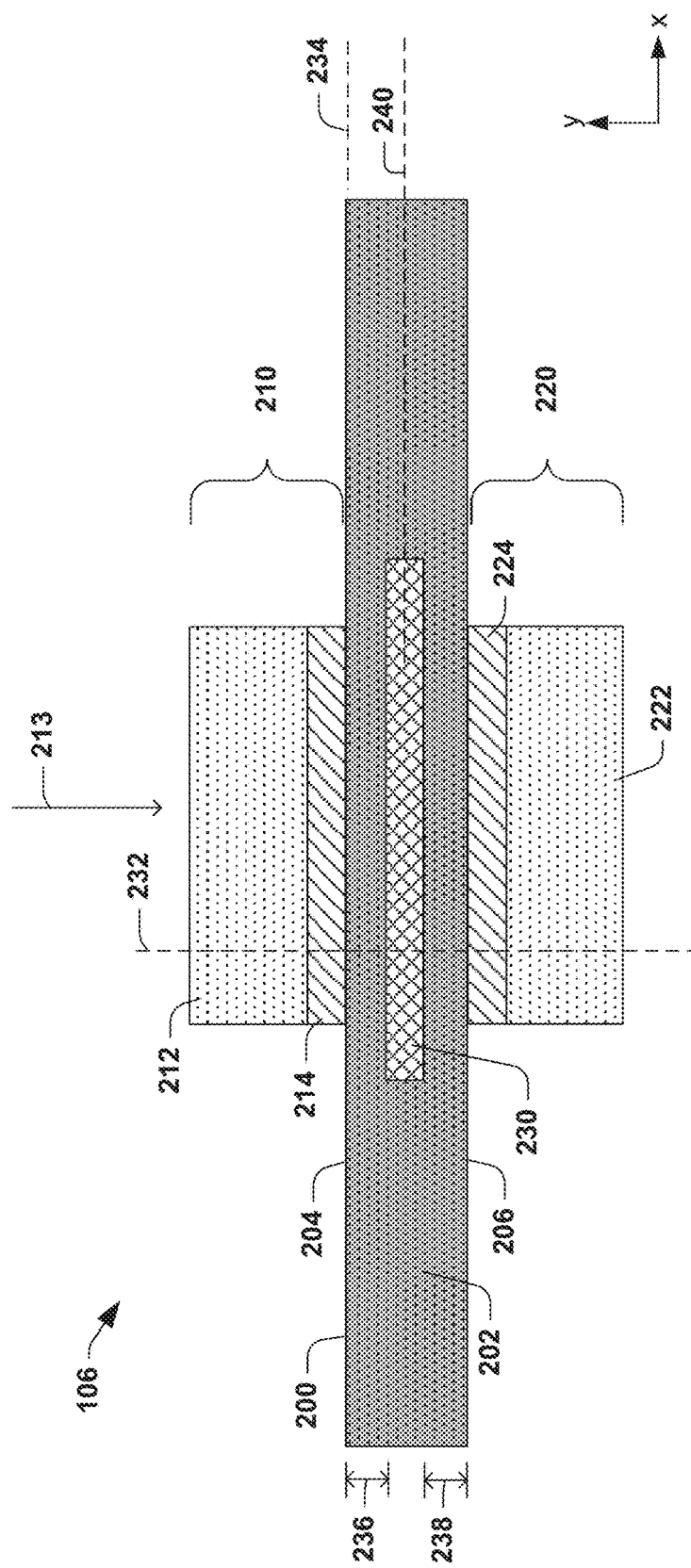
FIG. 2 illustrates a cross-sectional view of a portion of an example dual-energy detector array.

Turning to FIG. 2, a cross-sectional view of a portion of the dual-energy detector array 106 is illustrated. As illustrated, the dual-energy detector array 106 comprises a circuit board assembly 200. The circuit board assembly 200 may comprise a dielectric portion 202 and a conductive portion (e.g., located on a surface of or embedded within the circuit board assembly 200). The dielectric portion 202 can comprise any number of materials that are electrically insulating and are resistant to the flow of electric current through the dielectric portion 202. In some examples, the dielectric portion 202 comprises a substrate onto which the conductive portion is applied. The dielectric portion 202 can comprise, for example, one or more of fiberglass, silicon dioxide, aluminum oxide, sapphire, etc. In an example, the circuit board assembly 200 can define a first side 204 and a second side 206.

The dual-energy detector array 106 comprises a first conversion package 210. The first conversion package 210 can be coupled (e.g., directly mounted) to the first side 204 of the circuit board assembly 200 by way of an electrical conductive adhesive, solder balls, wire bond, etc. By being coupled to the first side 204 of the circuit board assembly 200, the first conversion package 210 can be attached to and/or electrically connected to the circuit board assembly 200. As such, electrical signals generated by the first conversion package 210 can be transmitted to the circuit board assembly 200, such as through conductive portions of the circuit board assembly 200.

The first conversion package 210 can directly or indirectly convert detected radiation photons into electrical charge. In an example, for indirect conversion, the first conversion package 210 comprises a first scintillator 212 and a first photodetector array 214. The first scintillator 212 can be positioned in a radiation pathway 213 between the circuit board assembly 200 and the radiation source 118. The radiation photons that impinge the first scintillator 212 can be converted into luminescent photons, which can be detected by a photodetector of the first photodetector array 214. In such an example, the first scintillator 212 can generate luminescent photons based upon the radiation photons impinging thereon. Example materials for the first scintillator 212 comprise, for example, Gadolinium Oxysulfide (GOS), Cadmium Tungstate, Bismuth Germanate, Cesium Iodide, Sodium Iodide, Lutetium Orthosilicate, Zinc selenide, Yttrium aluminum garnet, Bismuth Germanate, etc.

The first photodetector array 214 may be in contact with the first side 204 of the circuit board assembly 200. By being in contact with the first side 204 of the circuit board assembly 200, the first photodetector array 214 can be attached to and/or electrically connected to the circuit board assembly 200. The first photodetector array 214 comprises one or more photodetectors configured to detect at least some of the luminescent photons and to generate the electrical charge based upon the at least some of the luminescent photons. Respective photodetectors of the first photodetector array 214 may comprise back-illuminated photodiodes and/or front-illuminated photodiodes, for example. When a photodetector of the first photodetector array 214 detects a luminescent photon impinging thereon, the photodetector generates electrical charge, and electrical current under continuous operation. The analog electrical can be periodically sampled to generate a digital signal. Accordingly, respective photodetectors of the first photodetector array 214 are configured to generate a signal indicative of the amount of light detected by the photodetector between samplings (e.g., which correlates to the amount of radiation detected within a region of the first photodetector array 214 spatially proximate (e.g., above) the photodetector).

It will be appreciated that the first conversion package 210 is not limited to comprising the first scintillator 212 and the first photodetector array 214. Rather, in another example, the first conversion package 210 may comprise a first direct conversion material that is configured to convert the radiation photons into electrical charge. Such first direct conversion materials may comprise amorphous selenium, cadmium zinc telluride (CdZnTe), cadmium telluride (CdTe), and/or silicon, for example. As such, the first conversion package 210 may indirectly convert or directly convert detected radiation photons into electrical charge.

The dual-energy detector array 106 comprises a second conversion package 220. The second conversion package 220 can be coupled to the second side 206 of the circuit board assembly 200. By being coupled to the second side 206 of the circuit board assembly 200, the second conversion package 220 can be attached to and/or electrically connected to the circuit board assembly 200. As such, electrical signals generated by the second conversion package 220 can be transmitted to the circuit board assembly 200, such as through conductive portions of the circuit board assembly 200.

The second conversion package 220 can directly or indirectly convert detected radiation photons into electrical charge. In an example, for indirect conversion, the second conversion package 220 comprises a second scintillator 222 and a second photodetector array 224. The second scintillator 222 can be positioned in a radiation pathway 213, with the circuit board assembly 200 positioned between the second scintillator 222 and the radiation source 118. The radiation photons that impinge the second scintillator 222 can be converted into luminescent photons, which can be detected by a photodetector of the second photodetector array 224. In such an example, the second scintillator 222 can generate luminescent photons based upon the radiation photons impinging thereon. Example materials for the second scintillator 222 comprise, for example, Gadolinium Oxysulfide (GOS), Cadmium Tungstate, Bismuth Germanate, Cesium Iodide, Sodium Iodide, Lutetium Orthosilicate, Zinc selenide, Yttrium aluminum garnet, Bismuth Germanate, etc.

The second photodetector array 224 may be in contact with the second side 206 of the circuit board assembly 200. By being in contact with the second side 206 of the circuit board assembly 200, the second photodetector array 224 can be attached to and/or electrically connected to the circuit board assembly 200. The second photodetector array 224 comprises one or more photodetectors configured to detect at least some of the luminescent photons and to generate the electrical charge based upon the at least some of the luminescent photons. Respective photodetectors of the second photodetector array 224 may comprise back-illuminated photodiodes and/or front-illuminated photodiodes, for example. When a photodetector of the second photodetector array 224 detects a luminescent photon impinging thereon, the photodetector generates electrical charge, and electrical current under continuous excitation. The electrical current can be periodically sampled to generate a digital signal. Accordingly, respective photodetectors of the second photodetector array 224 are configured to generate an analog signal indicative of the amount of light detected by the photodetector between samplings (e.g., which correlates to the amount of radiation detected, between samplings, within a region of the second photodetector array 224 spatially proximate (e.g., above) the photodetector).

It will be appreciated that the second conversion package 220 is not limited to comprising the second scintillator 222 and the second photodetector array 224. Rather, in another example, the second conversion package 220 may comprise a second direct conversion material that is configured to convert the radiation photons into electrical charge. Such second direct conversion materials may comprise amorphous selenium, cadmium zinc telluride (CdZnTe), cadmium telluride (CdTe), and/or silicon, for example. As such, the second conversion package 220 may indirectly convert or directly convert detected radiation photons into electrical charge.

In an example, the dual-energy detector array 106 comprises a radiation filtering material 230 disposed within the circuit board assembly 200. The radiation filtering material 230 can be disposed between the first conversion package 210 and the second conversion package 220. In a possible example, an axis 232 can intersect the first conversion package 210 and the second conversion package 220. The axis 232 can extend in a direction that is substantially perpendicular to a plane 234 defined by a side (e.g., the first side 204 or the second side 206) of the circuit board assembly 200. In this example, the axis 232 can intersect the radiation filtering material 230 while intersecting the first conversion package 210 and the second conversion package 220. In the illustrated example, the radiation filtering material 230 can have a cross-sectional size (e.g., as measured along a filtering plane 240) that is equal to or greater than a cross-sectional size of the first conversion package 210 and/or the second conversion package 220. As such, in a possible example, any axis that intersects the first conversion package 210 and the second conversion package 220 that is substantially perpendicular to the plane 234 can intersect the radiation filtering material 230.

In this example, the radiation filtering material 230 can attenuate at least some of the radiation photons impinging thereon. That is, in such an example, the radiation filtering material 230 can inhibit the passage of at least some of the radiation photons through the radiation filtering material 230. In some examples, the radiation filtering material 230 comprises copper, tin, iron, zinc, silver, etc.

The radiation filtering material 230 can be at least partially embedded within the dielectric portion 202 of the circuit board assembly 200. For example, the radiation filtering material 230 can be spaced a first distance 236 from the first side 204 of the circuit board assembly 200. The radiation filtering material 230 can be spaced a second distance 238 from the second side 206 of the circuit board assembly 200. In some examples, the first distance 236 is substantially equal to the second distance 238, though, in other examples, the first distance 236 can be greater than or less than the second distance 238. In this example, the radiation filtering material 230 can extend along the filtering plane 240 that is substantially parallel to the plane 234 along which the circuit board assembly 200 extends.

In operation, the radiation filtering material 230 can attenuate at least some of the radiation photons impinging thereon to distance the effective photon energy of the first conversion package from the effective photon energy of the second conversion package. For example, if the radiation filtering material 230 where not present an effective photon energy of the first conversion package 210 may be about 60 keV while the effective photon energy of the second conversion package 220 may be about 100 keV (e.g., where the difference between the effective photon energies is primarily due to the first conversion package 210 filtering photons on the lower side of an emitted radiation photon). With the addition of the radiation filtering material 230, the second effective photon energy may increase to about 120 keV due to additional beam hardening provided by the radiation filtering material 230.

Figure 3:
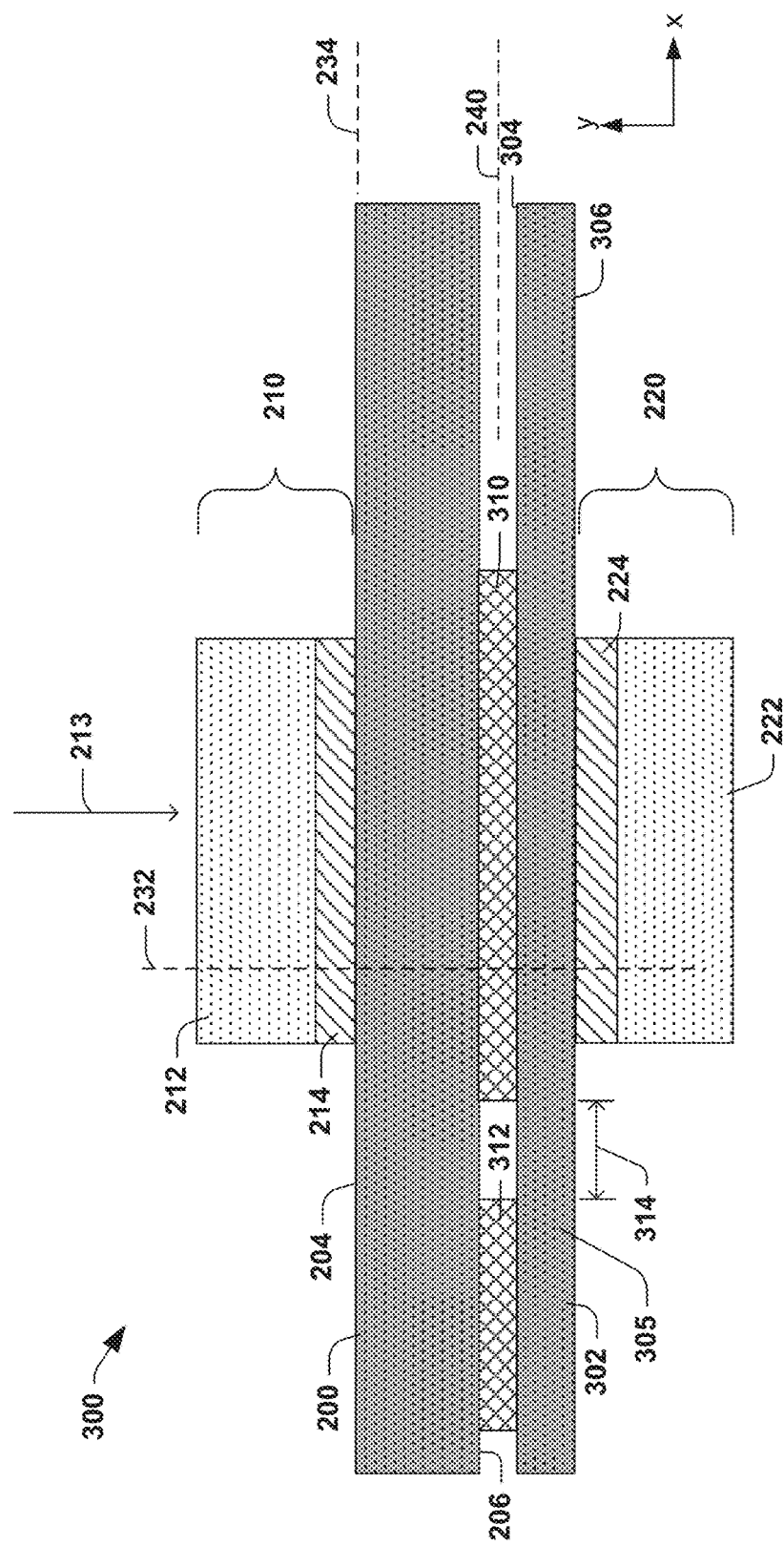
FIG. 3 illustrates a cross-sectional view of a portion of an example dual-energy detector array.

Turning to FIG. 3, a second example dual-energy detector array 300 is illustrated. The dual-energy detector array 300 may comprise the circuit board assembly 200, the first conversion package 210, the second conversion package 220, etc. In this example, the dual-energy detector array 300 comprises a second circuit board assembly 302. The second circuit board assembly 302 has a third side 304 and a fourth side 306. The second circuit board assembly 302 can comprise a dielectric portion 305 and a conductive portion. The dielectric portion 305 can comprise any number of materials that are electrically insulating and are resistant to the flow of electric current through the dielectric portion. In some examples, the dielectric portion 305 comprises a substrate onto which the conductive portion is applied. The dielectric portion 305 can comprise, for example, one or more of fiberglass, silicon dioxide, aluminum oxide, sapphire, etc.

The second conversion package 220 can be coupled to the fourth side 306 of the second circuit board assembly 302. By being coupled to the fourth side 306 of the second circuit board assembly 302, the second conversion package 220 can be attached to and/or electrically connected to the second circuit board assembly 302. In the illustrated example, the second photodetector array 224 can be in contact with the fourth side 306 of the second circuit board assembly 302. As such, electrical signals generated by the second conversion package 220 can be transmitted to the second circuit board assembly 302, such as through conductive portions of the second circuit board assembly 302.

The dual-energy detector array 300 comprises a radiation filtering material 310 coupled to the second side 206 of the circuit board assembly 200 and/or the third side 304 of the second circuit board assembly 302. In the illustrated example, the radiation filtering material 310 can be attached to and/or electrically connected to the second side 206 of the circuit board assembly 200 and the third side 304 of the second circuit board assembly 302. However, in other examples, the radiation filtering material 310 can be attached to and/or electrically connected to one of the second side 206 of the circuit board assembly 200 or the third side 304 of the second circuit board assembly 302.

The radiation filtering material 310 can be disposed between the first conversion package 210 and the second conversion package 220. In a possible example, the axis 232 can intersect the first conversion package 210, the second conversion package 220, and the radiation filtering material 310. As such, any axis 232 that intersects the first conversion package 210 and the second conversion package 220 that is substantially perpendicular to the plane 234 can intersect the radiation filtering material 310.

In this example, the radiation filtering material 310 can attenuate at least some of the radiation photons impinging thereon. That is, in such an example, the radiation filtering material 310 can inhibit the passage of at least some of the radiation photons through the radiation filtering material 310. In some examples, the radiation filtering material 310 comprises a conductive material that is capable of attenuating radiation photons, such as solder or the like.

The dual-energy detector array 300 can comprise a second radiation filtering material 312 coupled to at least one of the second side 206 of the circuit board assembly 200 or the third side 304 of the second circuit board assembly 302. In the illustrated example, the second radiation filtering material 312 can be attached to and/or electrically connected to the second side 206 of the circuit board assembly 200 and the third side 304 of the second circuit board assembly 302. However, in other examples, the second radiation filtering material 312 can be attached to and/or electrically connected to one of the second side 206 of the circuit board assembly 200 or the third side 304 of the second circuit board assembly 302.

In this example, the second radiation filtering material 312 may not be disposed between the first conversion package 210 and the second conversion package 220. Rather, the second radiation filtering material 312 may be spaced a separating distance 314 from the radiation filtering material 310. In a possible example, the axis 232 that intersects the first conversion package 210 and the second conversion package 220 may not intersect the second radiation filtering material 312. In this example, the second radiation filtering material 312 may comprise a conductive material that is capable of attenuating radiation photons, such as solder or the like.

The radiation filtering material 310 and/or the second radiation filtering material 312 can, at least in part, define an electrical path from at least one of the first conversion package 210 or the second conversion package 220. In a possible example, an electrical path may be defined from second circuit board assembly 302 to the circuit board assembly 200, which may comprise the data acquisition component. Such an electrical path may include the radiation filtering material 310 and/or the second radiation filtering material 312 (e.g., which can define an electrical pathway(s) between the second circuit board assembly 302 and the circuit board assembly 200. As such, in an example, the radiation filtering material 310 can simultaneously function to attenuate radiation photons and define an electrical path for electrical signals.

Figure 4:
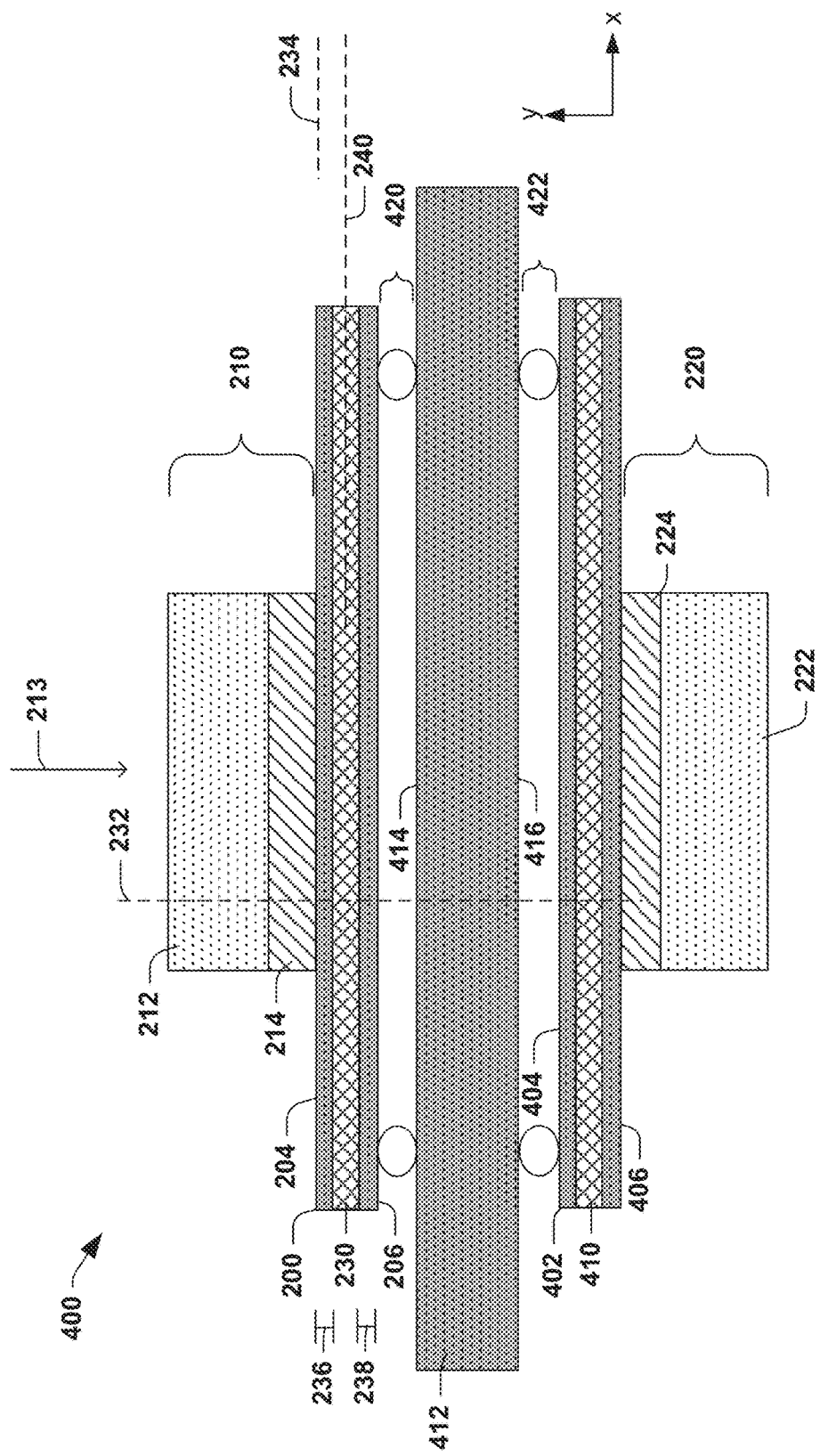
FIG. 4 illustrates a cross-sectional view of a portion of an example dual-energy detector array.

Turning to FIG. 4, a third example dual-energy detector array 400 is illustrated. The dual-energy detector array 400 may comprise the circuit board assembly 200, the first conversion package 210, the second conversion package 220, etc. In this example, the radiation filtering material 230 can be disposed between the first conversion package 210 and the second conversion package 220. For example, the radiation filtering material 230 can be disposed within (e.g., at least partially embedded within) the circuit board assembly 200. In an example, the axis 232 can intersect the first conversion package 210, the second conversion package 220, and the radiation filtering material 230. As such, any axis 232 that intersects the first conversion package 210 and the second conversion package 220 that is substantially perpendicular to the plane 234 can intersect the radiation filtering material 230.

The dual-energy detector array 400 comprises a second circuit board assembly 402 having a third side 404 and a fourth side 406. In an example, the third side 404 of the second circuit board assembly 402 can be coupled to the second side 206 of the circuit board assembly 200. By being coupled, it will be appreciated that the second circuit board assembly 402 may or may not be directly connected to the circuit board assembly 200. In the illustrated example, the second circuit board assembly 402 may be indirectly connected to the circuit board assembly 200, with one or more intervening layers between the third side 404 of the second circuit board assembly 402 and the second side 206 of the circuit board assembly 200. In other examples, the second circuit board assembly 402 may be directly connected to the circuit board assembly 200, without intervening layers in between.

The dual-energy detector array 400 comprises a second radiation filtering material 410 disposed within (e.g., at least partially embedded within) the second circuit board assembly 402. In an example, the axis 232 can intersect the first conversion package 210, the second conversion package 220, and the second radiation filtering material 410. As such, any axis 232 that intersects the first conversion package 210 and the second conversion package 220 that is substantially perpendicular to the plane 234 can intersect the second radiation filtering material 410.

The dual-energy detector array 400 comprises a third circuit board assembly 412 disposed between the circuit board assembly 200 and the second circuit board assembly 402. The third circuit board assembly 412 comprises a fifth side 414 and a sixth side 416. The fifth side 414 of the third circuit board assembly 412 can be coupled to the second side 206 of the circuit board assembly 200. The sixth side 416 of the third circuit board assembly 412 can be coupled to the third side 404 of the second circuit board assembly 402. In an example, one or more electrical connectors 420 can couple the circuit board assembly 200 to the third circuit board assembly 412. One or more second electrical connectors 422 can couple the second circuit board assembly 402 to the third circuit board assembly 412. In an example, the electrical connectors 420 and/or the second electrical connectors 422 can comprise electrically conductive materials, such as solder, or the like. In operation, the radiation filtering material 230 and the second radiation filtering material 410 can attenuate at least some of the radiation photons impinging thereon.

Figure 5:
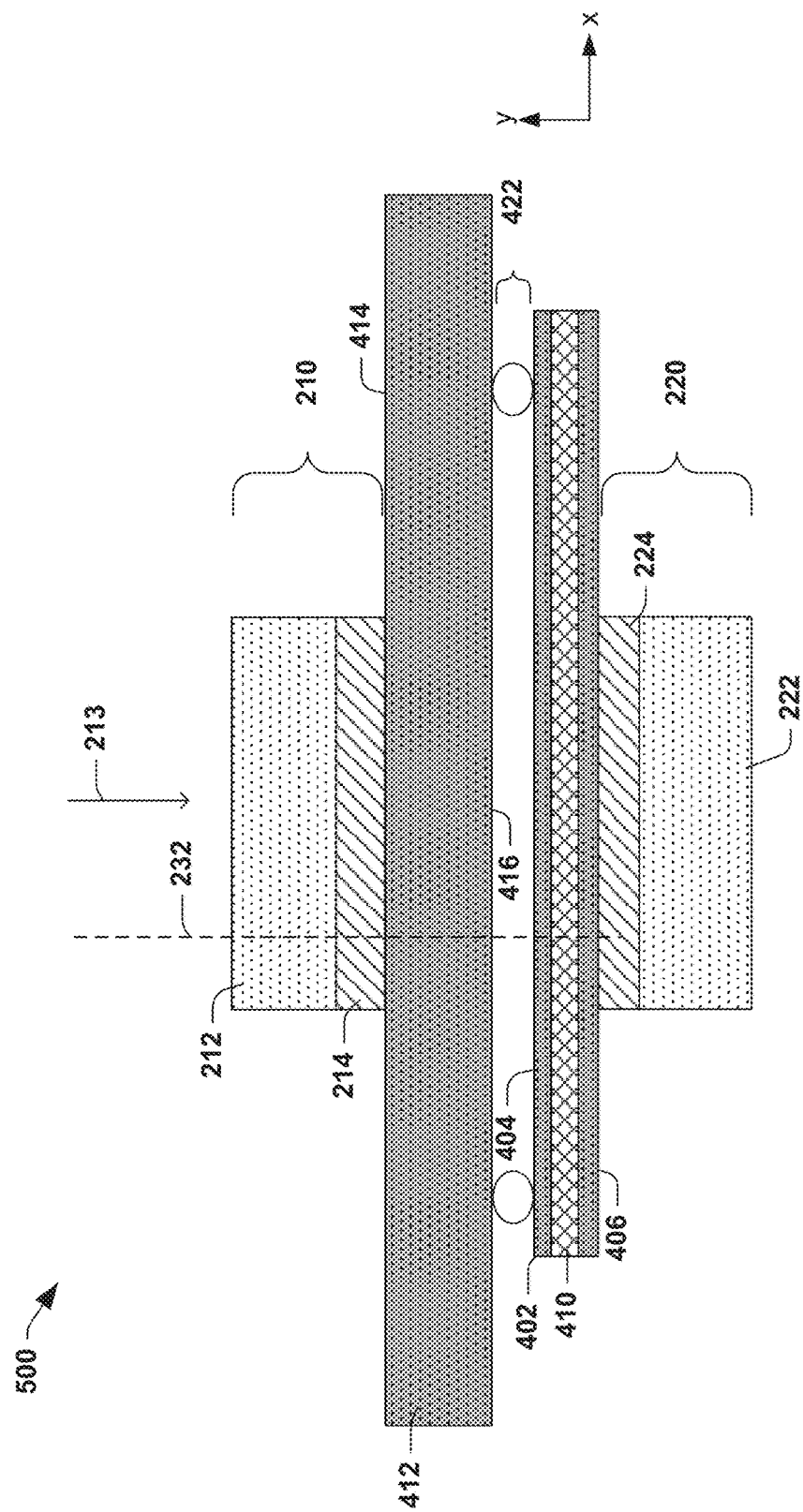
FIG. 5 illustrates a cross-sectional view of a portion of an example dual-energy detector array.

Turning to FIG. 5, a fourth example dual-energy detector array 500 is illustrated. The dual-energy detector array 500 may comprise the first conversion package 210, the second conversion package 220, the second circuit board assembly 402, the third circuit board assembly 412, etc. In this example, the dual-energy detector array 500 comprises two circuit board assemblies. For example, the first conversion package 210 can be coupled to the fifth side 414 of the third circuit board assembly 412. The second conversion package 220 can be coupled to the fourth side of the second circuit board assembly 402. It will be appreciated that the dual-energy detector array 500 is not limited to comprising the second circuit board assembly 402 and the third circuit board assembly 412. In another example, the second conversion package 220 can be coupled to the sixth side 416 of the third circuit board assembly 412. In such an example, the first conversion package 210 can be coupled to the first side 204 of the circuit board assembly 200. The fifth side 414 of the third circuit board assembly 412 can be coupled to the second side 206 of the circuit board assembly 200.

As used in this application, the terms "component", "module," "system", "interface", and the like are generally intended to refer to a computer-related entity, either hardware, a combination of hardware and software, software, or software in execution. For example, a component includes a process running on a processor, a processor, an object, an executable, a thread of execution, a program, or a computer. By way of illustration, both an application running on a controller and the controller can be a component. One or more components residing within a process or thread of execution and a component may be localized on one computer or distributed between two or more computers.

Moreover, "exemplary" is used herein to mean serving as an example, instance, illustration, etc., and not necessarily as advantageous. As used in this application, "or" is intended to mean an inclusive "or" rather than an exclusive "or". In addition, "a" and "an" as used in this application are generally be construed to mean "one or more" unless specified otherwise or clear from context to be directed to a singular form. Also, at least one of A and B and/or the like generally means A or B and/or both A and B. Furthermore, to the extent that "includes", "having", "has", "with", or variants thereof are used, such terms are intended to be inclusive in a manner similar to the term "comprising".

Many modifications may be made to the instant disclosure without departing from the scope or spirit of the claimed subject matter. Unless specified otherwise, "first," "second," or the like are not intended to imply a temporal aspect, a spatial aspect, an ordering, etc. Rather, such terms are merely used as identifiers, names, etc. for features, elements, items, etc. For example, a first set of information and a second set of information generally correspond to set of information A and set of information B or two different or two identical sets of information or the same set of information.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

What is claimed is:

1. A dual-energy detector array for a radiation system, the dual-energy detector array comprising:
    a circuit board assembly having a first side and a second side, the circuit board assembly comprising a dielectric portion and a conductive portion embedded within the dielectric portion;
    a first conversion package coupled to the first side of the circuit board assembly and having a first effective photon energy, the first conversion package having a first exposed surface configured to extend in a direction perpendicular to radiation;
    a second conversion package coupled to the second side of the circuit board assembly and having a second effective photon energy, the second conversion package having a second exposed surface configured to extend in the direction perpendicular to the radiation; and
    a radiation filtering material embedded within the dielectric portion of the circuit board assembly between the first conversion package and the second conversion package, the radiation filtering material configured to attenuate at least some radiation photons impinging thereon, wherein all sides of the radiation filtering material are surrounded by the dielectric portion of the circuit board assembly.

2. The dual-energy detector array of claim 1, wherein the first conversion package comprises:
    a first scintillator configured to generate luminescent photons based upon the radiation photons impinging thereon; and
    a first photodetector array comprising one or more photodetectors configured to detect at least some of the luminescent photons and to generate an electrical charge based upon the at least some of the luminescent photons, the first photodetector array in contact with the first side of the circuit board assembly.

3. The dual-energy detector array of claim 2, wherein the second conversion package comprises:
    a second scintillator configured to generate luminescent photons based upon the radiation photons impinging thereon; and
    a second photodetector array comprising one or more photodetectors configured to detect at least some of the luminescent photons and to generate the electrical charge based upon the at least some of the luminescent photons, the second photodetector array in contact with the second side of the circuit board assembly.

4. The dual-energy detector array of claim 1, wherein the first conversion package comprises a first direct conversion material.

5. The dual-energy detector array of claim 4, wherein the second conversion package comprises a second direct conversion material.

6. The dual-energy detector array of claim 1, wherein an axis intersecting the first conversion package and the second conversion package intersects the radiation filtering material, the axis substantially perpendicular to a plane defined by the first side of the circuit board assembly, further comprising another radiation filtering material within the circuit board assembly and laterally offset from the radiation filtering material.

7. The dual-energy detector array of claim 1, wherein the radiation filtering material comprises copper.

8. The dual-energy detector array of claim 1, wherein the radiation filtering material is spaced a first distance from the first side of the circuit board assembly and spaced a second distance from the second side of the circuit board assembly, the second distance different than the first distance.

9. A dual-energy detector array for a radiation system, the dual-energy detector array comprising:
    a first circuit board assembly having a first side and a second side;
    a second circuit board assembly having a third side and a fourth side;
    a first conversion package coupled to the first side of the first circuit board assembly and having a first effective photon energy;
    a second conversion package coupled to the fourth side of the second circuit board assembly and having a second effective photon energy;
    a first radiation filtering material coupled to the second side of the first circuit board assembly and the third side of the second circuit board assembly, the first radiation filtering material disposed between the first conversion package and the second conversion package, the first radiation filtering material configured to attenuate at least some radiation photons impinging thereon; and
    a second radiation filtering material coupled to the second side of the first circuit board assembly and the third side of the second circuit board assembly, the second radiation filtering material coplanar with the first radiation filtering material, the second radiation filtering material offset from scintillators of the first conversion package and from scintillators of the second conversation package, the second radiation filtering material defining an electrical path between the second side of the first circuit board assembly and the third side of the second circuit board assembly.

10. The dual-energy detector array of claim 9, wherein the first radiation filtering material defines a first electrical path from at least one of the first conversion package or the second conversion package.

11. The dual-energy detector array of claim 9, wherein an axis intersecting the second radiation filtering material does not intersect the scintillators of the first conversion package or the scintillators of the second conversion package, the axis substantially perpendicular to a plane defined by the first side of the first circuit board assembly.

12. A dual-energy detector array for a radiation system, the dual-energy detector array comprising:
   a first circuit board assembly having a first side and a second side;
   a second circuit board assembly having a third side and a fourth side, the third side of the second circuit board assembly coupled to the second side of the first circuit board assembly;
   a first conversion package coupled to the first side of the first circuit board assembly and having a first effective photon energy;
   a second conversion package coupled to the second circuit board assembly and having a second effective photon energy;
   a radiation filtering material disposed within the first circuit board assembly and embedded within the first circuit board assembly, the radiation filtering material configured to attenuate at least some radiation photons impinging thereon; and
   a third circuit board assembly between the first circuit board assembly and the second circuit board assembly, the third circuit board assembly not including a radiation filtering material.

13. The dual-energy detector array of claim 12, further comprising a second radiation filtering material disposed within the second circuit board assembly, the second circuit board assembly disposed between the first conversion package and the second conversion package.

14. The dual-energy detector array of claim 12, wherein the third circuit board assembly is coupled to the second side of the first circuit board assembly and the third side of the second circuit board assembly.

15. A radiation system comprising:
   a radiation source configured to emit radiation photons; and
   a dual-energy detector array comprising:
      a circuit board assembly having a first side and a second side;
      a first conversion package coupled to the first side of the circuit board assembly and having a first effective photon energy;
      a second conversion package coupled to the second side of the circuit board assembly and having a second effective photon energy; and
      a radiation filtering material disposed within the circuit board assembly between the first conversion package and the second conversion package, the radiation filtering material comprising a single unitary material configured to attenuate at least some of the radiation photons impinging thereon, the radiation filtering material embedded within a dielectric portion of the circuit board assembly.

16. The radiation system of claim 15, wherein the radiation filtering material defines a first electrical path from at least one of the first conversion package or the second conversion package.

17. The radiation system of claim 15, further comprising another radiation filtering material located within the circuit board assembly and laterally offset from the radiation filtering material.

* * * * *